(12) United States Patent
Jimenez (10) Patent No.: US 9,849,268 B2
(45) Date of Patent: Dec. 26, 2017

(54) CATHETER HAVING FLAT BEAM DEFLECTION TIP WITH FIBER PULLER MEMBERS

(71) Applicant: Biosense Webster (Israel), Ltd., Yokneam (IL)

(72) Inventor: Jose Jimenez, Ontario, CA (US)

(73) Assignee: BIOSENSE WEBSTER (ISRAEL), LTD., Yokneam (IL)

( * ) Notice: Subject to any disclaimer, the term of this patent is extended or adjusted under 35 U.S.C. 154(b) by 382 days.

(21) Appl. No.: 13/761,037

(22) Filed: Feb. 6, 2013

(65) Prior Publication Data

US 2014/0221920 A1    Aug. 7, 2014

(51) Int. Cl.
*A61M 25/01* (2006.01)
*A61M 25/00* (2006.01)

(52) U.S. Cl.
CPC .... *A61M 25/0147* (2013.01); *A61M 25/0144* (2013.01); *A61M 25/0009* (2013.01); *A61M 2025/015* (2013.01)

(58) Field of Classification Search
CPC .......... A61M 25/0133; A61M 25/0147; A61M 25/0105; A61M 2025/015; H01R 4/01; H01R 4/10; H01R 4/187
USPC .............................................. 604/95.04, 528
See application file for complete search history.

(56) References Cited

U.S. PATENT DOCUMENTS

| | | | |
|---|---|---|---|
| 4,963,699 A * | 10/1990 | Urushibata | H01R 12/778 174/72 A |
| RE34,502 E | 1/1994 | Webster, Jr. | |
| 5,334,145 A | 8/1994 | Lundquist et al. | |
| 5,357,979 A | 10/1994 | Imran | |
| 5,480,382 A | 1/1996 | Hammerslag et al. | |
| 5,827,278 A * | 10/1998 | Webster, Jr. | 606/41 |
| 5,891,088 A * | 4/1999 | Thompson et al. | 604/95.04 |
| 7,011,655 B2 * | 3/2006 | Thompson et al. | 604/529 |
| 7,048,711 B2 | 5/2006 | Rosenman et al. | |
| 7,594,903 B2 | 9/2009 | Webler et al. | |
| 2002/0162683 A1 * | 11/2002 | Fujiwara | 174/74 R |
| 2007/0156133 A1 | 7/2007 | McDaniel et al. | |

(Continued)

FOREIGN PATENT DOCUMENTS

| EP | 1 690 564 A1 | 8/2006 |
|---|---|---|
| EP | 2 165 730 A1 | 3/2010 |

(Continued)

OTHER PUBLICATIONS

EP Communication dated Apr. 14, 2014 and Extended European Search Report for European Application No. EP 14153915, 9 pgs.

*Primary Examiner* — Laura Bouchelle
(74) *Attorney, Agent, or Firm* — Roberts Mlotkowski Safran Cole & Calderon, P.C.

(57) ABSTRACT

A catheter has a metal deflection beam with rectangular cross-section and one or two fiber puller members for predictable on-plane bi-directional deflection. Each fiber puller member is anchored at its distal end to a respective surface of the beam by a metal ferrule that is crimped onto the distal end. The ferrule is shaped to provide a flat outer underside that can lie flat against a beam surface and a thin planar distal section that is welded to the beam. With a distal end of the beam sandwiched between the thin planar distal section of two ferrules, the ferrules and the beam can be welded together by a single laser pulse.

17 Claims, 9 Drawing Sheets

(56) References Cited

U.S. PATENT DOCUMENTS

2011/0270172 A1* 11/2011 Selkee .................. 604/95.04
2012/0172703 A1* 7/2012 Esguerra et al. ............ 600/409

FOREIGN PATENT DOCUMENTS

| EP | 2 172 240 A1 | 4/2010 |
| JP | 2008-245766 | 10/2008 |
| WO | WO 2006/135774 A1 | 12/2006 |
| WO | WO 2010/035599 A1 | 4/2010 |

* cited by examiner

CATHETER HAVING FLAT BEAM DEFLECTION TIP WITH FIBER PULLER MEMBERS

FIELD OF INVENTION

The present invention relates to a medical device for use in the vessel of a patient for the purpose of diagnosing or treating the patient, such as mapping tissue and/or ablating tissue using radio frequency (RF) or other sources of energy. More particularly, the invention relates to a deflectable catheter having a flat beam for on-plane bi-directional deflection.

BACKGROUND

Electrode catheters have been in common use in medical practice for many years. They are used to stimulate and map electrical activity in the heart and to ablate sites of aberrant electrical activity. In use, the electrode catheter is inserted into a guiding sheath which has been positioned in a major vein or artery, e.g., femoral artery, and guided into a chamber of the heart. Within the chamber, the catheter is extended past a distal end of the guiding sheath to expose the mapping assembly. The catheter is maneuvered through movements so that the mapping assembly is positioned at the tubular region in the heart chamber. The ability to control the exact position and orientation of the catheter is critical and largely determines how useful the catheter is.

Steerable catheters are generally well-known. For example, U.S. Pat. No. Re 34,502 describes a catheter having a control handle comprising a housing having a piston chamber at its distal end. A piston is mounted in the piston chamber and is afforded lengthwise movement. The proximal end of the elongated catheter body is attached to the piston. A puller wire is attached to the housing and extends through the piston, through the catheter body, and into a tip section at the distal end of the catheter body. In this arrangement, lengthwise movement of the piston relative to the housing results in deflection of the catheter tip section. The design described in U.S. Pat. No. RE 34,502 is generally limited to a catheter having a single puller wire. If bi-directional deflection is desire, more than one puller wire becomes necessary.

Catheters adapted for on-plane bi-directional deflection are also known. A flat beam is normally provided to enable deflection on both sides of the beam sweeping a defined plane. Metal flat deflection beams with shape memory are preferred and typically used in combination with metal puller wires. With this arrangement, anchoring of the metal puller wire on the metal deflection beam can be readily accomplished by use of a metal ferrule that is crimped onto a distal end of a metal puller wire and resistance welded with a flat metal wire to form a T-bar which is then resistance welded to the beam. However, metal and stainless steel puller wires and especially those constructed of Nitinol can be costly and weakened when crimped thus making them prone to breakage. Moreover, a catheter using fiber-based puller members can provide users with a smoother "feel" when manipulating deflection of the catheter. Some fiber-based puller members can also withstand a higher pull force than metal puller wires.

Thus, there is a desire for a catheter that employs the combination of a metal deflection beam and fiber-based puller members and provides a structure by which the fiber-based puller members can be readily and securely anchored to the metal beam.

SUMMARY OF THE INVENTION

The present invention is directed to a catheter having a metal deflection beam and one or more fiber puller members to effectuate predictable on-plane bi-directional deflection. The challenge of affixing or anchoring a nonmetal, fiber puller member onto a metal deflection beam is addressed by the use of a metal ferrule that is crimped onto a distal end of the fiber puller member and shaped with a flat outer underside and a thin planar distal portion, where the flat outer underside allows the ferrule to lie flat against the beam and the thin planar portion is resistance or laser welded to the beam at or near its distal end. Where the catheter has two fiber puller members for bi-directional deflection, the respective ferrules are positioned opposite and in mirror image of each other with a distal portion of the beam sandwiched in between. Each ferrule has its underside flat against a respective side of the beam and their respective thin planar distal portions are aligned such that both thin distal portions and the portion of the beam in between are welded together by a single laser pulse.

In one embodiment, the catheter comprises an elongated catheter body with a first tubular structure having first central lumen, a deflectable section distal of the catheter body and having a second tubular structure having a second central lumen, and a control handle proximal of the catheter body. For on-plane deflection, the catheter further includes a flat beam having first and second opposing surfaces, the flat beam extending through at least the second central lumen of the deflectable section, and at least one fiber puller member extending from the catheter body and through the deflectable section, alongside one surface of the flat beam. A ferrule is provided to anchor a distal end of the fiber puller member to the first surface of the beam. The ferrule provides a lumen receiving the distal end of the fiber puller member which extends only through a proximal portion of the ferrule, leaving the distal portion of the ferrule free of the fiber puller member and any other debris or contaminants. The crimped ferrule also has a shaped body providing a flat outer underside adapted to abut against the first surface of the beam and a thin planar distal portion that is welded to the beam by a single laser pulse.

In another embodiment, the catheter includes a second fiber puller member extending from the catheter body and through the deflectable section for on-plane bidirectional deflection. A second ferrule is provided to anchor a distal end of the second fiber puller member to the second surface of the beam. Like the first ferrule, the second ferrule provides a lumen receiving the distal end of the second puller member which extends only through a proximal portion of the second ferrule, leaving the distal portion of the second ferrule free of the second fiber puller member and any other debris or contaminants. The second crimped ferrule also has a shaped body providing a flat outer underside adapted to abut against the second surface of the beam and a thin planar distal portion, wherein the first and second thin planar distal portions are welded to the beam simultaneously by the single laser pulse.

In a more detailed embodiment, the proximal portion of the ferrule is crimped with teeth adapted to grip the distal end of the fiber puller member. The fiber puller members comprise fibers spun from a liquid crystal polymer and the deflection beam comprises at least one material selected from the group consisting of stainless steel alloys, nickel/titanium alloys and phosphor bronze alloys. The ferrule comprises stainless steel.

BRIEF DESCRIPTION OF THE DRAWINGS

These and other features and advantages of the present invention will be better understood by reference to the following detailed description when considered in conjunction with the accompanying drawings. It is understood that selected structures and features have not been shown in certain drawings so as to provide better viewing of the remaining structures and features.

DETAILED DESCRIPTION OF THE INVENTION

Figure 1:
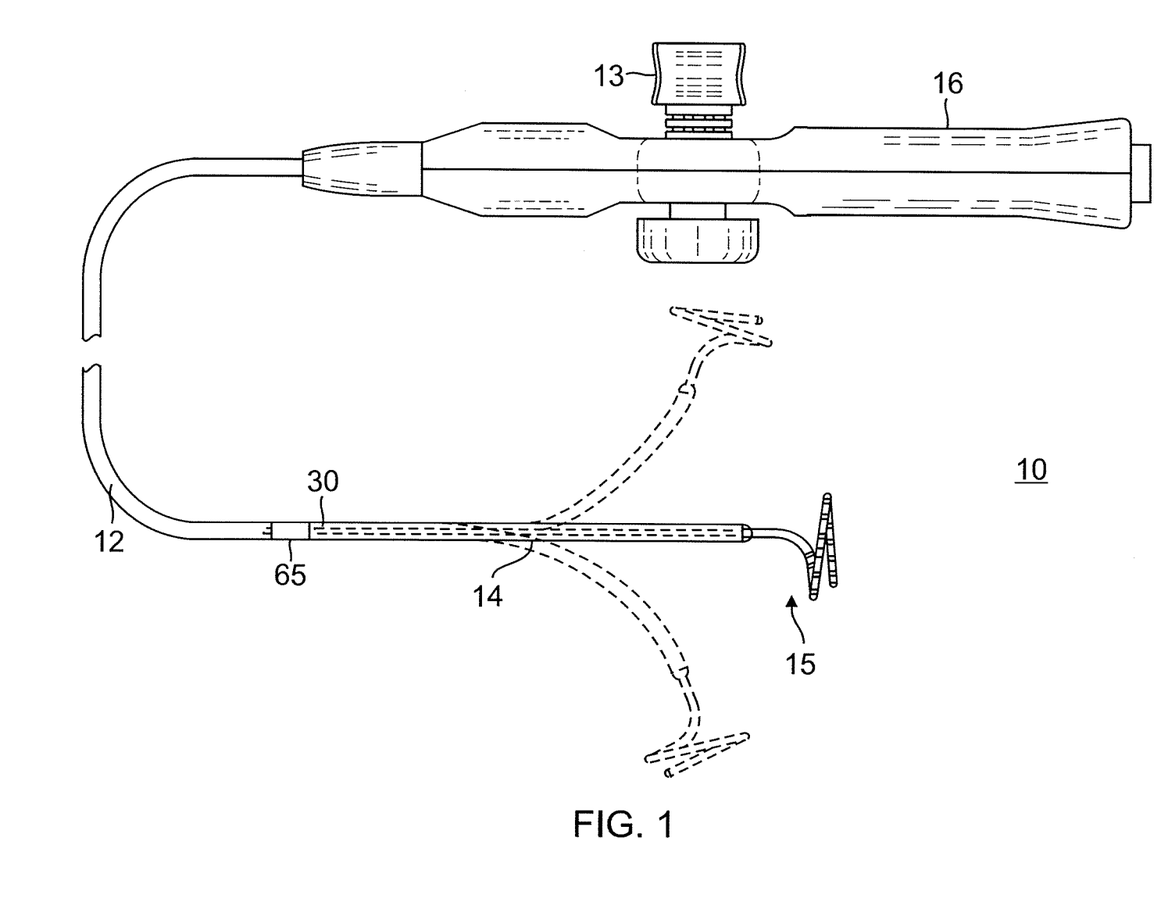
FIG. 1 is a top plan view of a catheter in accordance with one embodiment of the present invention.

The present invention is directed to a catheter having a catheter body (or shaft) and a deflectable distal portion having an elongated flat beam or "blade" that is deflected by one or more fiber puller members to effectuate precise on-plane bi-directional deflection. The use of the flat beam maximizes space within the catheter for components, including lead wires, puller wires, cables, tubings and any other support members for advanced distal tip designs. The use of the fiber puller members avoids breakage and weakness issues associated with puller wires. With reference to FIG. 1, a catheter 10 in accordance with an embodiment of the present invention includes a catheter body 12, a deflectable distal section 14 distal of the catheter body, and a control handle 16 proximal of the catheter shaft. The deflectable section 14 has a tip assembly 15 having, for example, a lasso design with a generally circular main portion extending and oriented transversely from a distal end of the deflectable section 14. Bi-directional deflection is effectuated by user manipulation of an actuator 13 provided on the control handle 16 which moves one or more puller members that extend along the catheter from the control handle 16 through the catheter body 12, and into the deflectable section 14.

Figure 2:
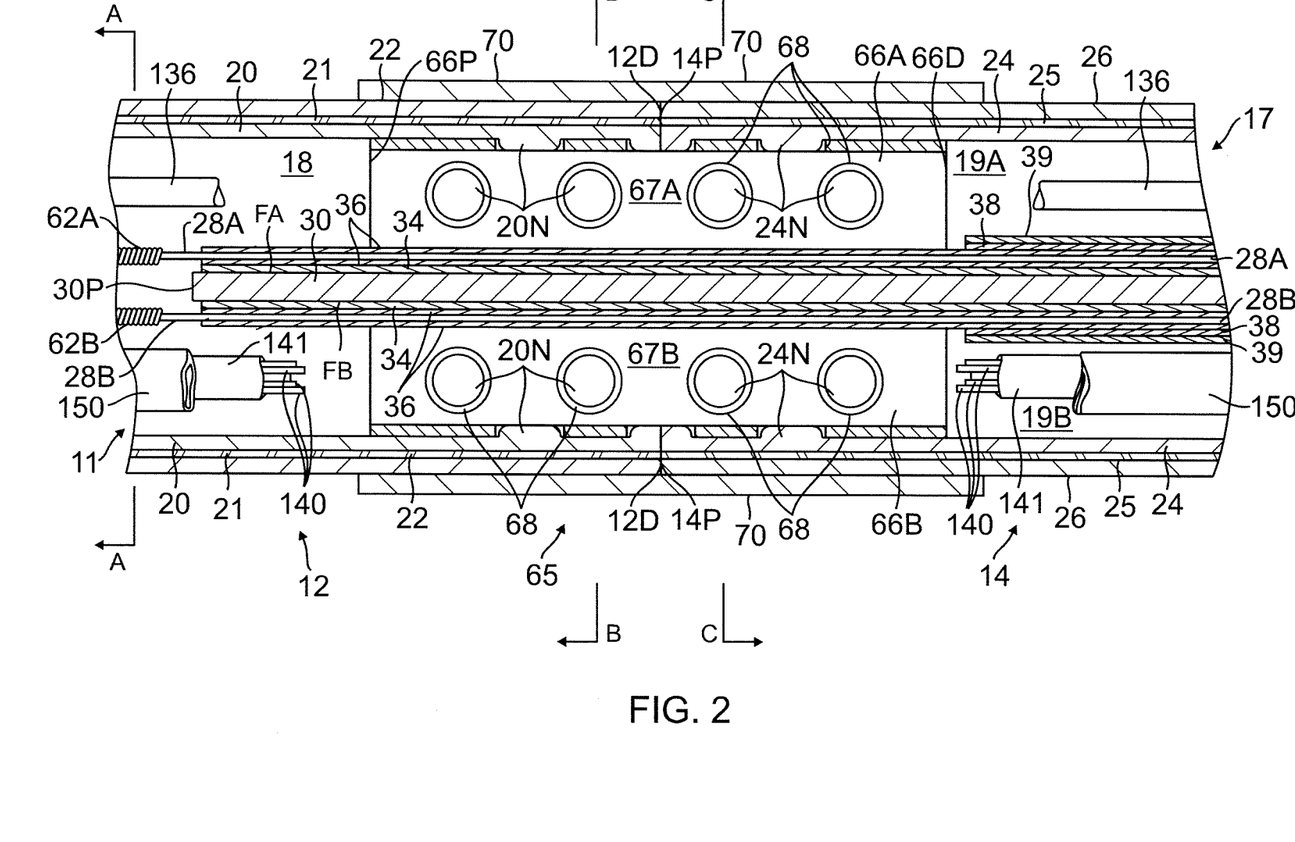
FIG. 2 is a side cross-sectional view of a transition section between a catheter body and a deflectable section of the catheter of FIG. 1 in accordance with one embodiment of the present invention.
Figure 2A:
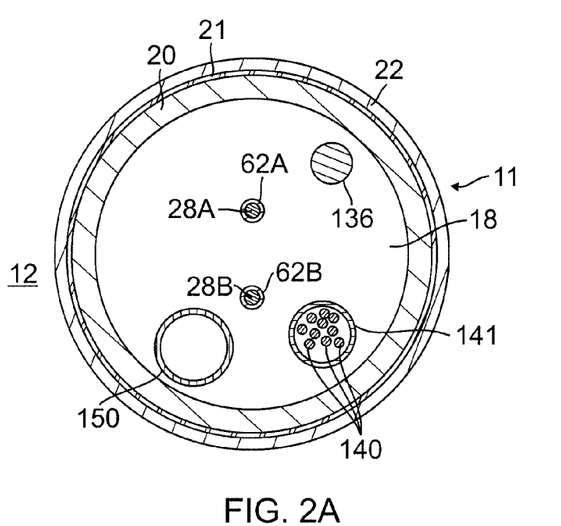
FIG. 2A is an end cross-sectional view of the catheter body of FIG. 2, taken along line C-C.

With reference to FIGS. 2 and 2A, the catheter body 12 is an elongated tubular structure 11 comprising a single, central or axial lumen 18. The catheter body 12 is flexible, i.e., bendable, but substantially non-compressible along its length. The catheter body 12 may be of any suitable construction and made of any suitable materials. In one embodiment, the catheter body 12 is multi-layered comprising at least an inner coat or layer 20, and an outer coat or layer 22 with an imbedded braided mesh 21 of stainless steel or the like to increase torsional stiffness of the catheter body 12 so that, when the control handle 16 is rotated, the deflectable section 14 of the catheter 10 rotates in a corresponding manner. The outer diameter of the catheter body 12 is not critical, but is preferably no more than about 8 French. Likewise the thicknesses of the layers 20 and 22 are not critical.

The deflectable section 14 has a tubular structure 17 with construction similar to the tubular structure 11 of the catheter body 12 except with greater flexibility. As shown in the embodiment of FIGS. 2 and 2C, the deflectable section 14 has a central lumen 19 and a multi-layered construction comprising at least an inner coat or layer 24, and an outer coat or layer 26 with an imbedded braided mesh 25 of stainless steel or the like. The outer diameter of the deflectable section 14 is similar to the catheter body 12, at preferably no more than about 8 French.

Suitable materials for the layers of the catheter body 12 and the deflectable section 14 include materials with moderate heat deflection temperatures so stiffness of the catheter body 12 and the deflectable section 14 and thus their deflection characteristics are not modified by introduction into the patient's body due to temperature variations. Suitable materials for the inner and outer layers 20 and 22 of the catheter body 12 include Pebax and Pellethane. Materials particularly suitable for both the inner and outer layers 20 and 22 include lower shore hardness plastics ranging from about 25-55D.

Suitable materials for the inner and outer layers 24 and 26 of deflectable section 14 include polyurethane or Pebax. In one embodiment, the tubular structure 17 of the deflectable section 14 includes an extruded braided structure, with the inner layer 24 having a thickness ranging between about 0.002 inch to 0.003 inch of natural "sticky" 2533-SA-01 PEBAX, then braided with 0.0016 inch diameter, PEN braid (50-80 pics per inch), and the outer layer 26 including extruded PEBAX 5533-SA-01 or 4031-SA-01 PEBAX with about 25% barium sulfate added for radiopacity.

Figure 2B:
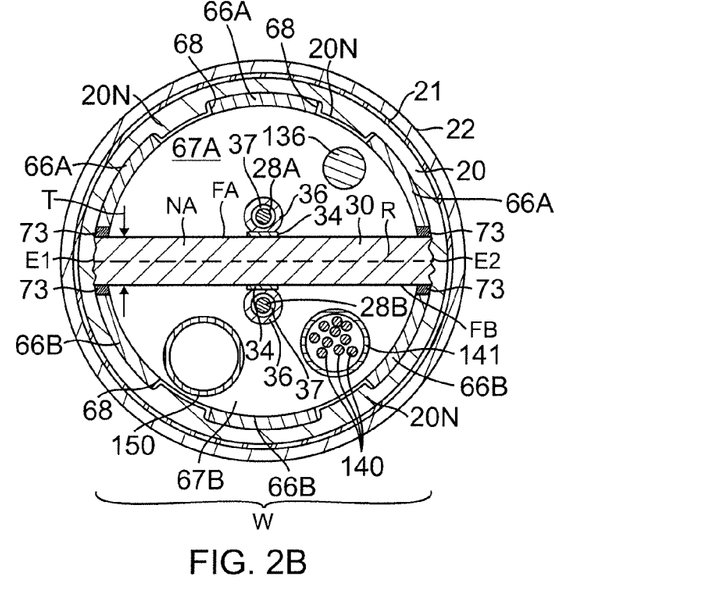
FIG. 2B is an end cross-sectional view of the transition section of FIG. 2, taken along line A-A.
Figure 2C:
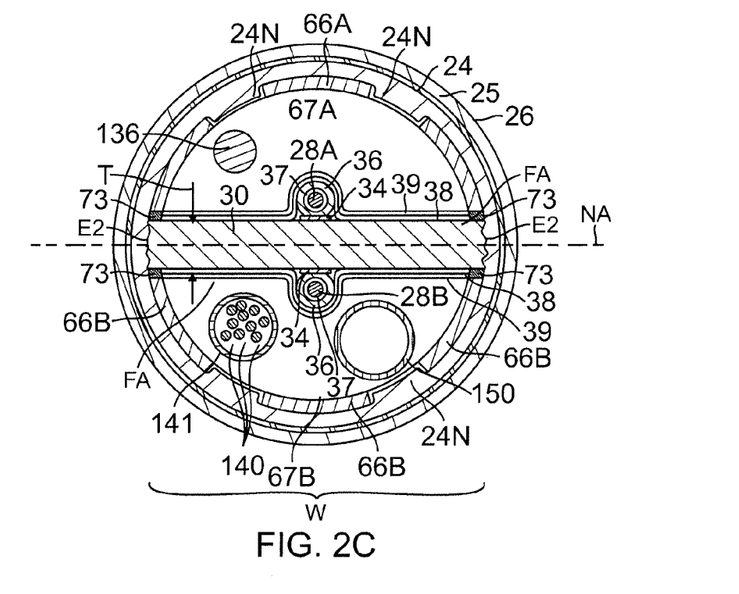
FIG. 2C is an end cross-sectional view of the transition section of FIG. 2, taken along line B-B.

Extending through the length of the deflectable section 14 is an elongated support structure configured as a flat beam or "blade" 30 with a rectangular cross-section R having a greater width W and a lesser thickness T, as shown in FIG. 2B, defining two opposing rectangular face surfaces FA and FB (or sides, used interchangeably herein) that are flat and smooth, and two outer longitudinal side edge surfaces E1 and E2 that are friction-inducing, e.g., uneven, rough, textured and/or serrated. The beam 30 may be constructed of any suitable high yield strength material that can be straightened or bent out of its original shape upon exertion of a force and is capable of substantially returning to its original shape upon removal of the force. Suitable materials for the beam include full hard, cold worked stainless steel alloys (304 or 316 full hard condition), nickel/titanium alloys (nitinol) or phosphor bronze alloys. Nitinol alloys typically comprise about 55% nickel and 45% titanium, but may comprise from about 54% to about 57% nickel with the balance being titanium. A suitable nickel/titanium alloy is nitinol, which has excellent shape memory, together with ductility, strength, corrosion resistance, electrical resistivity and temperature stability. The width W of the beam generally equals the inner diameter of the deflectable section 14. Accordingly, the beam 30 is situated inside the deflectable section 14 to effectively divide or bisect the central lumen 19 into two sub-lumens, e.g., equal half cylindrical spaces 19A and 19B, with components such as lead wires, cables, and tubings passing through either space.

Figure 3:
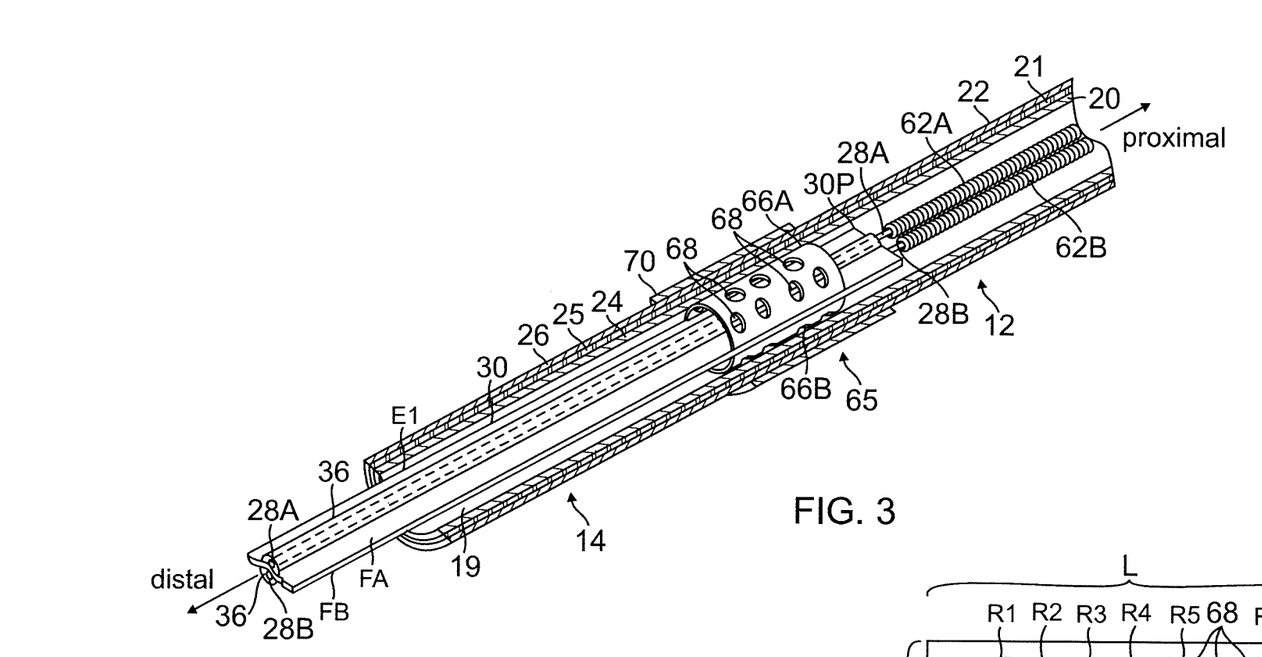
FIG. 3 is a perspective view of the transitional section of FIG. 2, shown partially broken away.
Figure 3A:
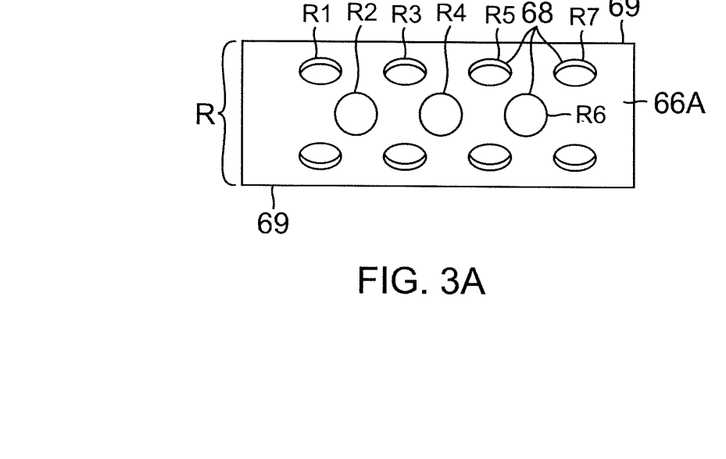
FIG. 3A is a top view of a joint bracket in accordance with one embodiment.

The catheter 10 has exceptional torque transmission capability provided by a joint or transition section 65 between the catheter shaft 12 and the deflectable section 14, as shown in FIGS. 2 and 3. The transition section 65 transfers torsional forces from the control handle 16 to the distal assembly 15 with high fidelity and low hysteresis, to provide a user with a means to accurately place and control the distal assembly 15 within the patient. The transition section 65 includes a pair of opposing, elongated half-cylindrical members or brackets 66A, 66B, e.g., formed by die cutting or acid etching, with circular perforations or punched through-holes 68 arranged in a predetermined pattern. In one embodiment, there are 11 through-holes and the pattern includes a plurality of transverse rows, with adjacent rows offset by a predetermined distance, although it is understood that other alternating or offset patterns would be suitable, as well. In the illustrated embodiment of FIG. 3A, the pattern has rows R1, R3, R5 and R7 with two through-holes each, and rows R2, R4 and R6 with one through-hole each, where rows R2, R4 and R6 are offset from rows 1, 3, 5 and 7 by about the diameter of a perforation. The brackets 66A, 66B can be constructed of the same material as the beam 30 and may be pre-coated with an adhesive for higher bond strength during heat fusion.

In the illustrated embodiment, each bracket has a uniform semi-circular or "C" shape cross section along its length and is affixed at its outer side edges 69, e.g., by laser welding 73, to a respective side of the beam 30. Having a curved or semi-circular cross-section, the C brackets 66A, 66B provide structural support to abutting ends of the tubular structures 11 and 17 at the transition section 65. As better shown in FIG. 3, the brackets 66A and 66B are affixed to the beam 30 near its proximal end 30P (which extends a short distance proximally past the joint 65 between the catheter body 12 and the deflectable section 14). So affixed, the brackets 66A and 66B generally form a cylindrical hollow body 66 (with a circumferential contour substantially encircling the beam 30 at the transition section 65) that defines a central lumen 67 that is bisected by the beam 30 into two semi-circular cavities 67A and 67B (FIGS. 2B and 2C) through which components, such as lead wires, cables, etc., can pass.

With reference to FIGS. 2 and 3, in assembling the catheter 10 and the transition section 65, a distal end 11D of the tubular structure 11 of the catheter shaft 12 is slid onto proximal end 66P of the cylindrical body 66. A proximal end 17P of the tubular structure 17 deflectable section 14 is slid onto distal end 66D of the cylindrical body 66, with the beam 30 extending through the lumen 19 of the deflectable section 14 (with a small proximal end of the beam 30 extending into the lumen 18 of the catheter body 12). Accordingly, distal end of the tubular structure 17 and proximal end of the tubular structure 11 cover the cylindrical body 66 from opposite directions such that they abut each other at or near a mid-location along the length of the body 66, which can range between about 5 mm and 12 mm, preferably about 6.5 mm and 10 mm.

The inner coatings 20 and 24 of the tubular structures 11 and 17, respectively, are then fused to the body 66, with application of sufficient heat and pressure so as to melt and flow into the perforations 68 forming nodes 20N and 24N (FIG. 2). The fusion creates a very strong interlocking bond between the tubular structures of the catheter shaft 12 and the deflectable section 14. The nodes 20N and 24N increase the axial load capacity to the joint 65. In fact, the resulting torque transmission bond joint can be stronger in torsion and tensile force loading than the braided catheter body 12 and deflection section 14 that are bonded to it. The friction-inducing edges E1 and E2 of the beam 30 within and in contact with the body 66 also help grab the inner layers 20 and 24 and prevent slippage between the beam 30 and the tubular structures 11 and 17.

To facilitate the application of heat and pressure to the transition section 65, one or more protective heat-shrink tubing 70 (FIG. 2), e.g., fluorinated ethylene propylene (FEP) or polyethylene terephthalate (PET), is placed and shrunken (or "recovered") over the transition section (e.g., by a heat gun or oven). The transition section 65 covered by the heat-shrink tubing(s) 70 is then placed in a two-piece heat fusing die head (not shown) for heating to melt (or "reflow") the inner layers 20 and 24 into the perforations 68, followed by cooling. The shrink tubing 70 can be used as a process aid to prevent the melted layers from contacting the heated die and create a uniform transition between mating ends of the deflectable section 14 and the catheter body 12. Thus, the shrink tubing(s) 70 are removed from the transition section 65 after the fusing process.

The heat fusing die head utilizes a highly accurate fusing die height measurement indicator (LVDT) to sense fusing die head movement during the heating/fusing process. Since the construction materials of the layers of the shaft 12 and the deflection section 14 may include extruded raw thermoplastic polymers with a wide range of heat histories (±25° F.) between material lots, monitoring the softening of the polymers and the resultant die head movement is another means besides temperature measurement to achieve process control while reducing the influence of polymer heat history during the heating/fusing process. Moreover, the transition section can be created in minimal duration (e.g., less than about 60 seconds) using a thermal fusing machine that is water-cooled to provide fast cycle times. The resulting transition section is advantageously homogenous and seamless. The structure is nondiversified once heat-pressure fuse operation is completed.

As also shown in FIGS. 2 and 3, the catheter 10 provides bi-directional deflection with a pair of fiber puller members 28A and 28B, each extending centrally along a respective face surface FA, FB of the beam 30. Because the puller members are not rigidly attached to the beam 30, this arrangement provides smooth bi-directional steering. A suitable material for the fiber puller members is VECTRAN, a manufactured fiber, spun from a liquid crystal polymer (LCP) created by Celanese Acetate LLC and now manufactured by Kuraray Co., Ltd. However, it is understood that other synthetic fibers or cordage may be used.

Proximal ends of the fiber puller members 28A and 28B are anchored in the control handle 16 and deflection mechanism in the control handle 16 responsive to the actuator 13 (FIG. 1) manipulated by a user is configured to draw or otherwise act on a proximal end of fiber puller members 28A or 28 to deflect the distal section 14 with a distinct curvature on side FA or FB of the beam 30. Throughout the catheter body 12, each fiber puller member extends through a respective compression coil 62A and 62B (FIGS. 2 and 3) which is flexible but resists compression so that deflection of the catheter initiates at or near distal ends of the compression coils. Along the beam 30 in the deflectable section 14, each fiber puller member may be coated with PTFE or Teflon so the puller members can slide smoothly inside a respective protective spacer tube 36 provided on a respective side of the beam 30 as discussed in further detail below.

With reference to FIG. 2C, each spacer 36 has a predetermined thickness to separate the puller members 28A and 28B and a neutral bending axis NA of the beam 30 by a predetermined distance so as to lower the force on the puller members, including the bending moment. In the illustrated embodiment, the spacer 36 on each side of the beam 30 may include a spacer adhesive layer 34 and a wall of a lumened elastomeric spacer tube 36. To constrain and secure the fiber puller members on the beam 30 and as an additional means to prevent adhesive failure and detachment, one or more heat shrink tubings 38 and 39 are placed on the beam 30, covering and surrounding the spacers on both sides FA and FB of the beam 30, inclusive of the fiber puller members 28A, 28B trained through the spacers. The roughened or texturized longitudinal edges E1 and E2 of the beam 30 help grab and secure the first heat shrink tubing 38 so it does not migrate or slip during deflection.

The heat shrink tubings 38 and 39 extend from the distal end 30D of the beam to near the distal end of the brackets 66A, 66B, so as not to interfere with the weld 73 between the 66A and 66B and the beam 30. Depending on the length of the beam 30 proximal of the brackets 66A, 66B, heat shrink tubings may be provided there as well.

Figure 4:
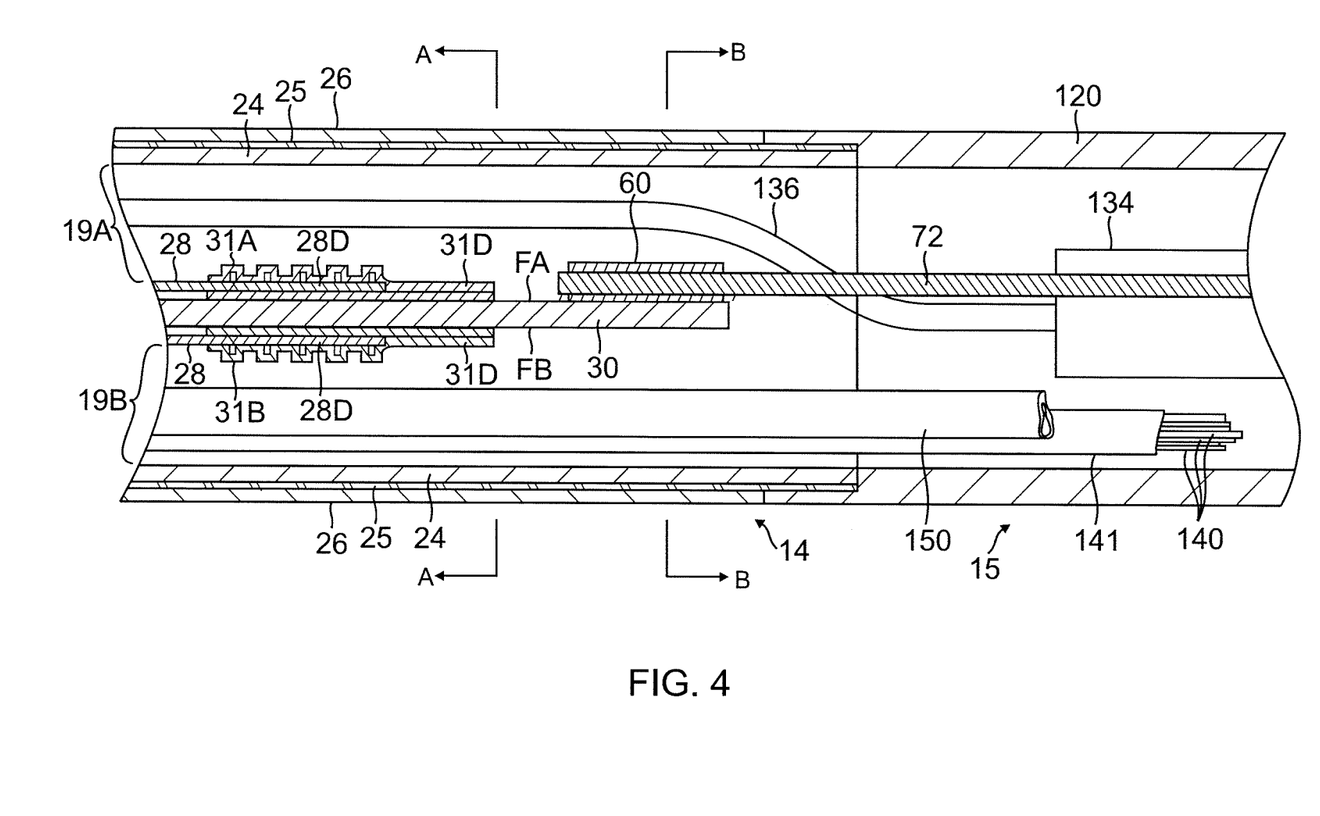
FIG. 4 is a side cross-sectional view of a junction between the deflectable section and a distal assembly of the catheter of FIG. 1, in accordance with an embodiment of the present invention.
Figure 4A:
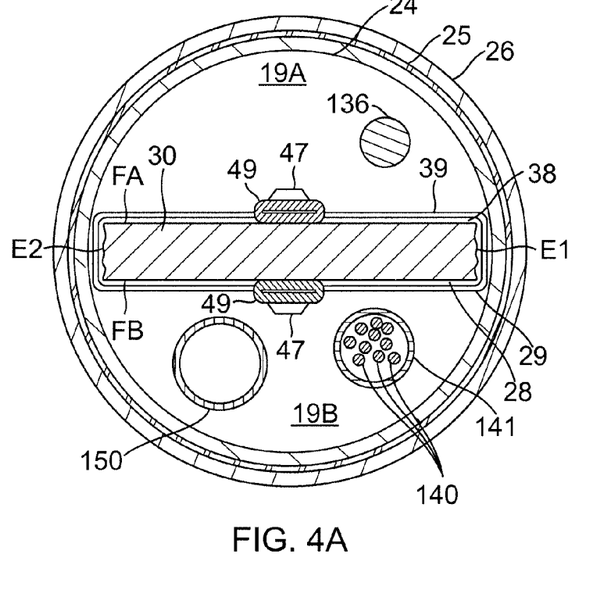
FIG. 4A is an end-cross sectional view of the deflectable section of FIG. 4, taken along line A-A.
Figure 4B:
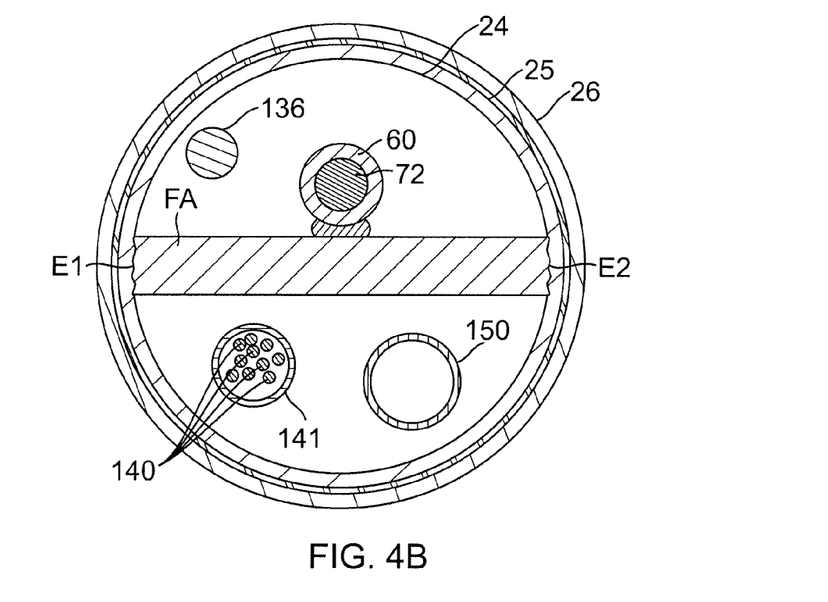
FIG. 4B is an end-cross sectional view of the deflectable section of FIG. 4, taken along line B-B.
Figure 5:
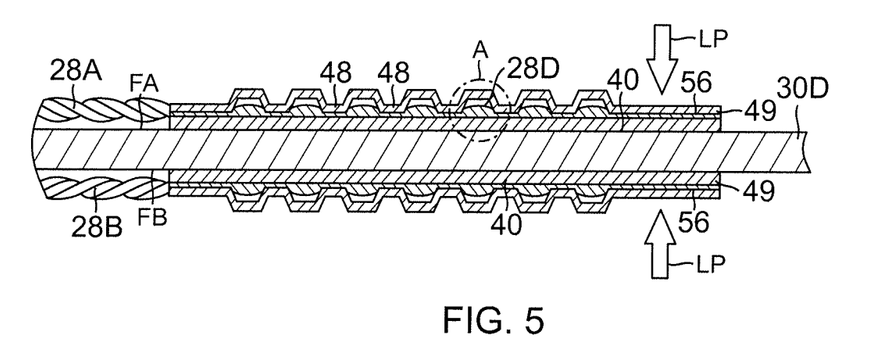
FIG. 5 is a side cross-sectional view of a distal portion of a deflection beam with distal ends of fiber puller members anchored thereon, in accordance with one embodiment of the present invention.
Figure 5A:
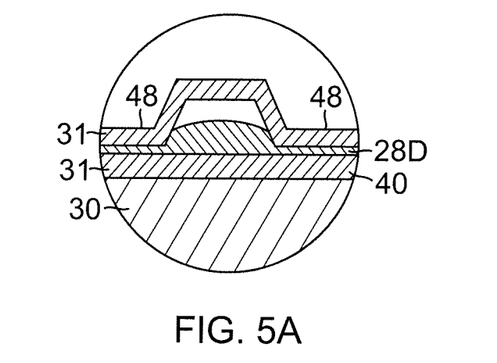
FIG. 5A is detailed view of a portion of the deflection beam of FIG. 5.

In accordance with a feature of the present invention, a metal ferrule or tube 31A and 31B, e.g., a hypodermic tubing of stainless steel or other alloys, is crimped and attached onto a distal end 28D of each fiber member 28A and 28B, as shown in FIGS. 4 and 5. Each ferrule has a hollow cylindrical body with a proximal portion 31P and a distal portion 31D. When stamped, coined or otherwise flattened with a puller member affixed thereto, the body forms an anchor that is welded to the beam 30 to fixedly secure the puller member to the beam 30. As explained below, the flattened body provides a flat underside 40 and a thin planar portion 49. The flat underside 40 allows the body to lie flat against the beam 30 and the thin planar portion 49 allows the body to be readily affixed, e.g., resistance- or laser-welded, to the beam.

Figures 6, 8:
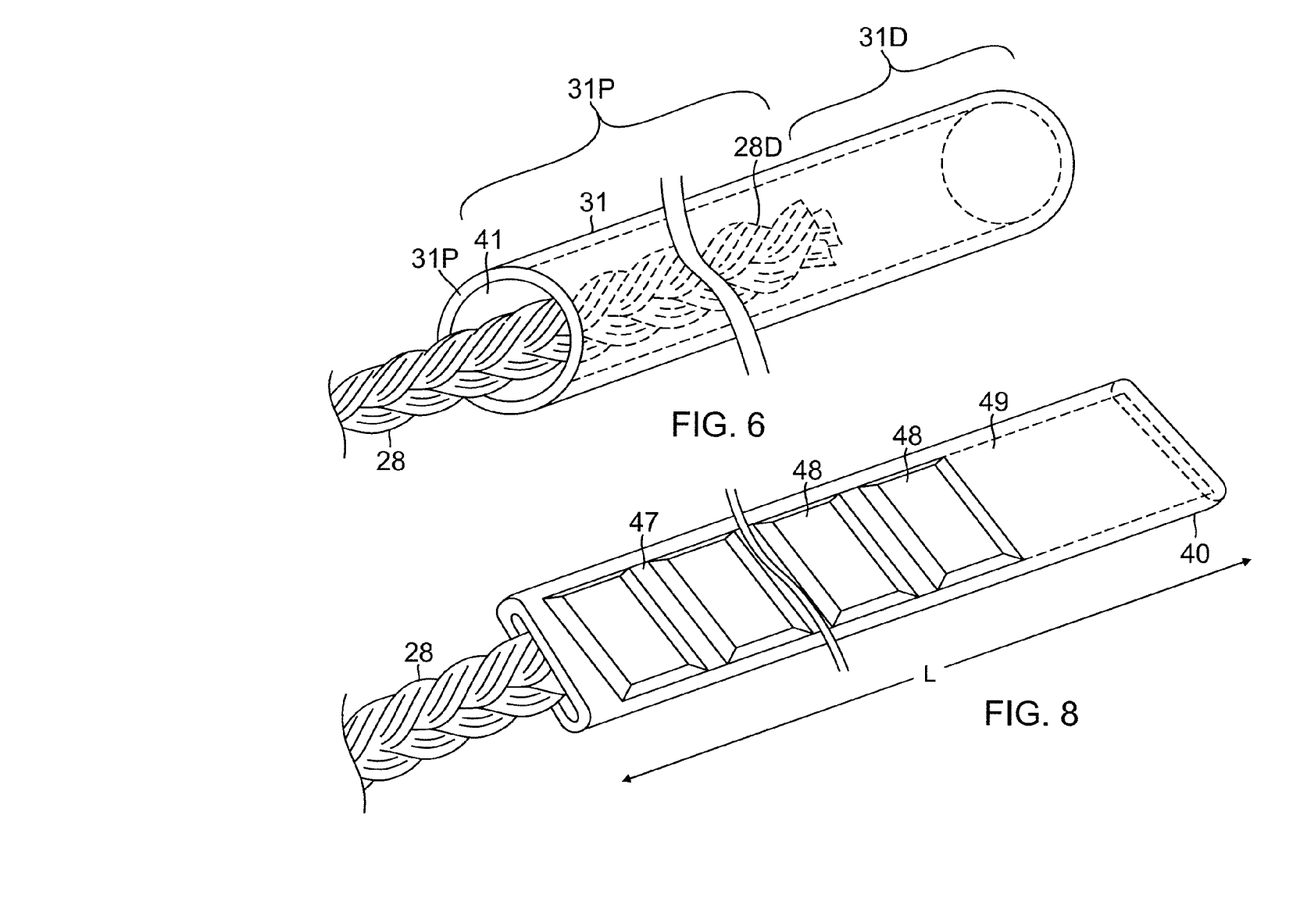
FIG. 6 is a perspective view of a ferrule prior to reshaping and flattening.
FIG. 8 is a perspective view of the ferrule of FIG. 6 after reshaping and flattening.

To prepare the ferrule for anchoring, a distal end 28D of each puller member 28 is inserted into a central lumen 41 of the ferrule 31 from its proximal end as shown in FIG. 6. Notably, the distal end 28D extends through the proximal portion 31P of the body only so that the distal portion 31D remains free and devoid of the puller member, and preferably of any other debris or contaminants. The distal portion 31D may range between about 10% and 30%, and preferably about 20% of the length L of the body. For example, a ferrule body having a length ranging between about 0.16 in and 0.2 in, the distal portion ranges between 0.032 in and 0.035 in.

Figure 7:
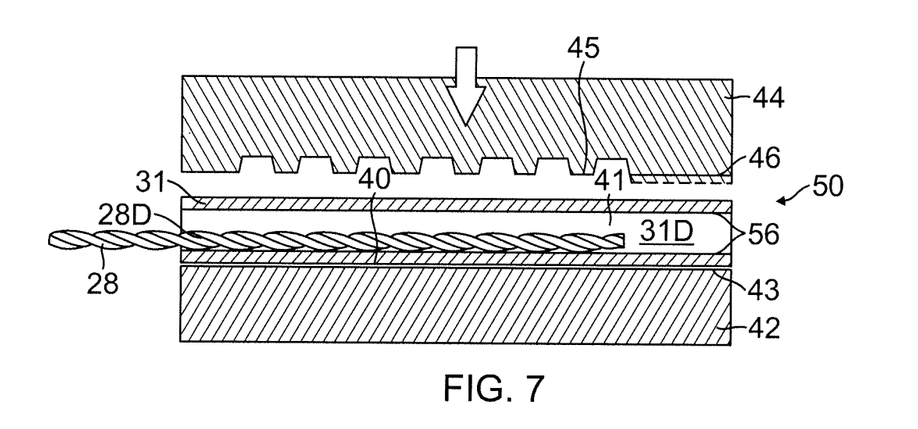
FIG. 7 is a side cross-sectional view of a ferrule prepared for stamping in a die set.
Figure 9:
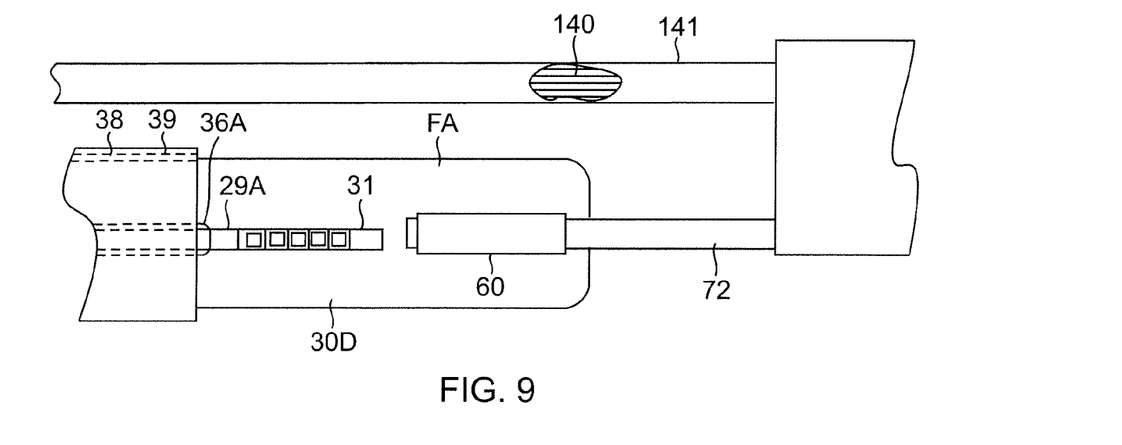
FIG. 9 is a top plan view of a distal end of a deflection beam of FIG. 4, with components of the distal assembly attached thereto, according to one embodiment of the present invention.

The entirety of the ferrule 31 (along with the inserted distal end 28D of the puller member) is placed in a die set 50 for coining or stamping. In the illustrated embodiment of FIG. 7, the die set 50 includes a confined die 42 and a movable punch 44 which are driven toward each other to stamp, coin or otherwise reshape the body of the ferrule. The confined die 42 has a flat surface 43 to form and shape the flat underside 40. The movable punch 44 has uneven formations 45 corresponding to the proximal portion 31D of the ferrule to crimp that portion of the ferrule onto the distal end 28D of the puller member. The uneven formations 45 form serrations or teeth 48 to clamp and grip the distal end 28D which then is fixedly secured in the lumen 41 of the stamped ferrule. The movable punch 44 also provides a flat surface 46 that corresponds with the distal portion 31D of the body which is formed and shaped into the thin planar portion 49 where inner surfaces 56 of the body are brought into contact with each other and being substantially free of contaminants or air gaps therebetween. In that regard, the flat surface 46 of the movable punch 44 may have a deeper projection or dimension toward the confined die 42 such that there is assurance of extremely close contact between the inner surfaces 56.

To anchor a stamped ferrule 31 to the beam 30, an assembly is formed with the beam in combination with either one coined ferrule 31 for unidirectional deflection or two coined ferrules 31A and 31B for bi-directional deflection. As shown in FIG. 5, the flat underside 40 of each stamped ferrule 31A and 31B is placed facing and in contact with a respective surface FA and FB of the beam 30. As such, the ferrules 31A and 31B are arranged in mirror image of each other where their flat undersides 40 are directed toward each other with the beam 30 sandwiched in between. So arranged with either one or two coined ferrules, the thin planar portions 49 are aligned with each other on opposite sides of the beam 30 so that the assembly can be welded together by means of a single laser pulse LP applied to a thin planar portion 49 from either side FA or FB of the beam 30. Notably, any air gap between the flat contacting surfaces of the beam 30 and each thin planar portion 49 should be no greater than about 0.002 inches in order to provide a robust oxide free weld zone that enables a single laser pulse to penetrate the planar portions 49A and 49B and the beam 30 and weld all three components together. The use and stamping of the ferrules advantageously allow nonmetal, fiber-based puller members to be used with a metal beam-based deflection and steering mechanism. It is understood that where the stamped ferrule(s) are mounted on the beam by resistance welding, each stamped ferrule may be welded singly and not simultaneously.

The fiber puller members 28, preferably excluding the distal ends 28D, may be coated with low density polyethylene or TEFLON, e.g., DUPONT TRASYS 9825 or TRASYS 426 and MCLUBE 1829 TEFLON based coatings, to damp out noise and prevent stick-slip type non-uniform motion created by variations in dynamic and static friction coefficients during deflection. Food grade damping gel (e.g., Nye Lubricants fluorocarbon Gel 835C-FG//874//880FG) having synthetic hydrocarbon and PTFE or silicone and PTFE to coat the fibers 29 and interior of the spacer tubes 36.

In the illustrated embodiment of FIG. 1, the distal assembly 15 comprises a generally straight proximal region and a generally circular main region having at least one loop circling about 360 degrees, if not two loops circling about 720 degrees. The proximal region is mounted on the deflectable section 14 and the main region carries a plurality of electrodes (ring and/or tip) for mapping and/or ablation.

With reference to FIG. 4, the distal assembly 15 includes the shape memory support member 72, lead wires 140 for the electrodes carried on the distal assembly 15, and a cover 120 extending the length of the distal assembly. The lead wires 140 attached to the electrodes on the distal assembly 15 extend through a nonconductive sheath 141 which extends from the distal assembly through the lumen half 19B of the deflectable section 14, through the cavity half 67B of the transition section 65, through the lumen 18 of the catheter shaft 12, and into the control handle 16. Ring electrodes may also be carried on the deflectable section 14.

An electromagnetic position sensor 134 (FIG. 4) is mounted in or near the distal end of the deflectable section 14 or the proximal end of the distal assembly 15. A sensor cable 136 extends from the sensor 134 into the half lumen 19A of the deflectable section 14, the cavity half 67B of the transition section 65, the central lumen 18 of the catheter body 12 and into the control handle 16 where it terminates in a suitable connector (not shown).

The catheter 10 may also be adapted for irrigation at the distal assembly 15, for example, to supply fluid at or near the electrodes of the distal assembly. To that end, an irrigation tubing 150 may be provided to pass fluid to the distal assembly 15 from the control handle 16. In the illustrated embodiment of FIG. 2, the tubing 150 passes through the central lumen 18 of the catheter body 12, the lumen 19b of the deflectable section 14, and into the distal assembly 15.

In use, a suitable guiding sheath is inserted into the patient with its distal end positioned at a desired location. An example of a suitable guiding sheath for use in connection with the present invention is the Preface™ Braiding Guiding Sheath, commercially available from Biosense Webster, Inc. (Diamond Bar, Calif.). The distal end of the sheath is guided into one of the chamber, for example, the atria. A catheter in accordance with an embodiment of the present invention is fed through the guiding sheath until its distal end extends out of the distal end of the guiding sheath. As the catheter is fed through the guiding sheath, the distal assembly 15 is straightened to fit through the sheath. Once the distal end of the catheter is positioned at the desired location, the guiding sheath is pulled proximally, allowing the deflectable section 14 and distal assembly 15 to extend outside the sheath, and the distal assembly 15 returns to its original shape due to its shape-memory.

The user manipulating the actuator 13 on the control handle 16 actuates deflection mechanism inside the control handle 16 to draw puller members 28A or 28B to deflect the distal section 14 on-plane to one or the other side of the beam 30. The user may then rotate the distal assembly 15 by rotating the control handle 16 which transfers torque to the catheter body 12 and the deflectable section 14 through the transition section 65. The brackets 66A and 66B to which the tubular structures 11 and 17 of the catheter body 12 and the deflectable section 14 are bonded by means of interlocking nodes formed in the perforations 68 of the brackets 66A and 66B under heat fusion.

Suitable materials for construction of the beam and/or the half-cylindrical brackets include 50/50NiTi, titanium (Ti-6AI-4V), phosphor bronze 510, beryllium copper, monel alloy K-500 or MP35N (a non-magnetic nickel-cobalt-chromium-molybdenum alloy). Suitable materials for imbedded braided mesh for the tubular structures of the catheter body and/or the deflectable section include stainless steel (304V or 316), phosphor bronze, monel K-500, PEN or other synthetic fibers that can readily bond with PEBAX or PELLETHANE extruded thermoplastics during the secondary/outer extrusion coat or layer.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter, comprising:
   an elongated catheter body comprising a first tubular structure having a first central lumen, a distal end and a proximal end;
   a deflectable section having a second tubular structure having a second central lumen, and a proximal end that is distal of the proximal end of the catheter body;
   a control handle proximal of the catheter body;
   a flat beam having first and second opposing surfaces, the flat beam extending through at least the second central lumen of the deflectable section and at least partially into the central lumen of the catheter body;
   first and second brackets defining a joint between the deflectable section and the catheter body, a portion of the flat beam extending through the first and second brackets, the first bracket being affixed to a first side of the flat beam, and the second bracket being affixed to a second side of the flat beam;
   at least one fiber puller member extending from the catheter body and through the deflectable section, the at least one fiber puller member having a distal end; and
   an anchor member anchoring the distal end of the at least one fiber puller member to the first surface of the beam, the anchor member having:
      a ferrule comprising:
         a lumen, the distal end of the at least one fiber puller member extending into the lumen and through only a proximal portion of the ferrule;
         a thin planar distal portion devoid of the fiber puller member; and
         a flat outer underside spanning both the thin planar distal portion and the proximal portion of the ferrule, the flat outer underside adapted to abut against the first surface of the beam; and
      a weld formation between the thin planar distal portion and the first surface of the beam.

2. The catheter of claim 1, wherein the proximal portion of the ferrule has teeth adapted to grip the distal end of the at least one fiber puller member.

3. The catheter of claim 1, wherein the weld formation is a single laser pulse weld formation.

4. The catheter of claim 1, further comprising:
   a second fiber puller member extending from the catheter body and through the deflectable section, the second fiber puller member having a distal end; and
   a second anchor member anchoring the distal end of the second fiber puller member to the second surface of the beam, the second anchor member having:
      a second ferrule comprising:
         a second lumen, the distal end of the second fiber puller member extending into the lumen and through only a proximal portion of the second ferrule, a second thin planar distal portion devoid of the second fiber puller member; and a second flat outer underside spanning both the second thin planar distal portion and the proximal portion of the second ferrule, the flat outer underside adapted to abut against the second surface of the beam; and a second weld formation between the second thin planar distal portion and the second surface of the beam.

5. The catheter of claim 4, wherein the proximal portion of the second ferrule has teeth to grip the distal end of the second fiber puller member.

6. The catheter of claim 1, wherein the at least one fiber puller member comprises a fiber spun from a liquid crystal polymer.

7. The catheter of claim 1, wherein the beam comprises at least one material selected from the group consisting of stainless steel alloys, nickel/titanium alloys and phosphor bronze alloys.

8. The catheter of claim 1, wherein the ferrule comprises stainless steel.

9. The catheter of claim 1, wherein the first weld formation is at or near a distal end of the beam.

10. The catheter of claim 4, wherein the second weld is at or near a distal end of the beam.

11. The catheter of claim 4, wherein the first and second weld formations are portions of one single laser pulse weld.

12. A catheter, comprising:
an elongated catheter body comprising a first tubular structure having a first central lumen, a distal end and a proximal end;
a deflectable section having a second tubular structure having a second central lumen, and a proximal end that is distal of the proximal end of the catheter body;
a control handle proximal of the catheter body;
a flat beam having first and second opposing surfaces, the flat beam extending through at least the second central lumen of the deflectable section and at least partially into the central lumen of the catheter body;
first and second brackets defining a joint between the deflectable section and the catheter body, a portion of the flat beam extending through the first and second brackets, the first bracket being affixed to a first side of the flat beam, and the second bracket being affixed to a second side of the flat beam;
first and second fiber puller members extending from the catheter body and through the deflectable section, each puller member having a respective distal end; and
first and second anchor members anchoring the distal end of the respective fiber puller member to the first and second surfaces, respectively, of the beam, each of the first and second anchor members having:
a ferrule comprising:
a lumen, the distal end of the respective puller member extending into the lumen and through only a proximal portion of the ferrule;
a thin planar distal portion devoid of the respective fiber puller member; and
a flat outer underside spanning both the thin planar distal portion and the proximal portion of the ferrule, the flat outer underside adapted to abut against the respective surface of the beam; and
a single laser pulse weld formation, a portion of the weld formation being between each thin planar distal portion and the respective surface of the beam.

13. The catheter of claim 12, wherein the proximal portion of each ferrule has teeth adapted to grip the distal end of the respective fiber puller member.

14. The catheter of claim 1, wherein the at least one fiber puller member comprises a fiber spun from a liquid crystal polymer.

15. The catheter of claim 1, wherein the beam comprises at least one material selected from the group consisting of stainless steel alloys, nickel/titanium alloys and phosphor bronze alloys.

16. The catheter of claim 12, wherein each ferrule comprises stainless steel.

17. The catheter of claim 1, wherein the single laser pulse weld formation is at or near a distal end of the beam.

* * * * *